US009551608B2

(12) United States Patent
Cho et al.

(10) Patent No.: US 9,551,608 B2
(45) Date of Patent: Jan. 24, 2017

(54) WEARABLE DEVICE AND METHOD FOR CONTROLLING THE SAME

(71) Applicant: LG ELECTRONICS INC., Seoul (KR)

(72) Inventors: Eunhyung Cho, Seoul (KR); Sinae Chun, Seoul (KR); Jongho Kim, Seoul (KR); Jihwan Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 418 days.

(21) Appl. No.: 14/176,753

(22) Filed: Feb. 10, 2014

(65) Prior Publication Data

US 2015/0149116 A1    May 28, 2015

(30) Foreign Application Priority Data

Nov. 27, 2013 (KR) .......................... 10-2013-0145079

(51) Int. Cl.
*G01G 9/00* (2006.01)
*A61B 5/00* (2006.01)
(Continued)

(52) U.S. Cl.
CPC ............... *G01G 9/00* (2013.01); *A61B 5/1107* (2013.01); *A61B 5/681* (2013.01); *G06K 9/00342* (2013.01); *G06Q 50/22* (2013.01); *A61B 5/01* (2013.01); *A61B 5/021* (2013.01); *A61B 5/026* (2013.01); *A61B 5/02438* (2013.01); *A61B 5/0404* (2013.01); *A61B 5/0476* (2013.01); *A61B 5/0488* (2013.01); *A61B 5/0531* (2013.01); *A61B 5/0816* (2013.01)

(58) Field of Classification Search
CPC ..... G01G 9/00; A61B 5/1107; A61B 5/02438; A61B 5/01; A61B 5/0476; A61B 5/0531; A61B 5/026; A61B 5/681; A61B 5/021; A61B 5/0404; A61B 5/0488; A61B 5/0816
USPC .... 702/173, 188; 600/301, 547; 340/539.12, 340/539.13, 573.1; 342/357.25
See application file for complete search history.

(56) References Cited

U.S. PATENT DOCUMENTS 7,219,923 B2 * 5/2007 Fujita ..................... B60N 2/002
280/735
8,021,297 B2 * 9/2011 Aerts ................... A61B 5/0205
600/300

(Continued)

FOREIGN PATENT DOCUMENTS

JP         2002-253301 A    9/2002
KR    10-2010-0122617 A   11/2010
WO    WO 2006/006092 A1    1/2006

*Primary Examiner* — Carol S Tsai
(74) *Attorney, Agent, or Firm* — Birch, Stewart, Kolasch & Birch, LLP

(57) ABSTRACT

A wearable device and a method for controlling the same are disclosed herein. The wearable device, comprising a bio-signal sensor unit configured to sense a bio-signal; a storage unit configured to store data; and a processor configured to control the bio-signal sensor unit and the storage unit, wherein the processor is further configured to: generate first reference data including a weight of a first reference object and a first bio-signal being generated by holding the first reference object when the first bio-signal is detected, generate measurement data including a second bio-signal being generated by holding a measurement object, when the second bio-signal is detected, and obtain a weight of the measurement object by comparing the measurement data with the first reference data.

19 Claims, 9 Drawing Sheets

(51) Int. Cl.

| | | |
|---|---|---|
| *A61B 5/11* | (2006.01) | |
| *G06K 9/00* | (2006.01) | |
| *G06Q 50/22* | (2012.01) | |
| *A61B 5/01* | (2006.01) | |
| *A61B 5/021* | (2006.01) | |
| *A61B 5/024* | (2006.01) | |
| *A61B 5/026* | (2006.01) | |
| *A61B 5/0404* | (2006.01) | |
| *A61B 5/0476* | (2006.01) | |
| *A61B 5/0488* | (2006.01) | |
| *A61B 5/053* | (2006.01) | |
| *A61B 5/08* | (2006.01) | |

(56) References Cited

U.S. PATENT DOCUMENTS

| | | | |
|---|---|---|---|
| 8,200,453 B2* | 6/2012 | Gage | G06F 19/3475 177/1 |
| 8,541,700 B2* | 9/2013 | Sato | G01G 23/3728 177/25.11 |
| 9,060,683 B2* | 6/2015 | Tran | A61B 5/0022 |
| 2004/0162702 A1* | 8/2004 | Pandipati | G01G 19/4146 702/173 |
| 2004/0245036 A1* | 12/2004 | Fujita | B60N 2/002 180/272 |
| 2009/0089672 A1* | 4/2009 | Tseng | A61B 5/0537 715/700 |
| 2009/0322513 A1* | 12/2009 | Hwang | A61B 5/02055 340/539.12 |
| 2011/0224505 A1* | 9/2011 | Sadhu | A61B 5/0006 600/301 |
| 2011/0295145 A1* | 12/2011 | Sato | A61B 5/0537 600/547 |
| 2011/0301916 A1* | 12/2011 | Oshima | G01G 19/50 702/173 |
| 2012/0330683 A1* | 12/2012 | Ledwidge | A61B 5/0002 705/3 |
| 2013/0131463 A1* | 5/2013 | Date | G01G 19/50 600/301 |

* cited by examiner

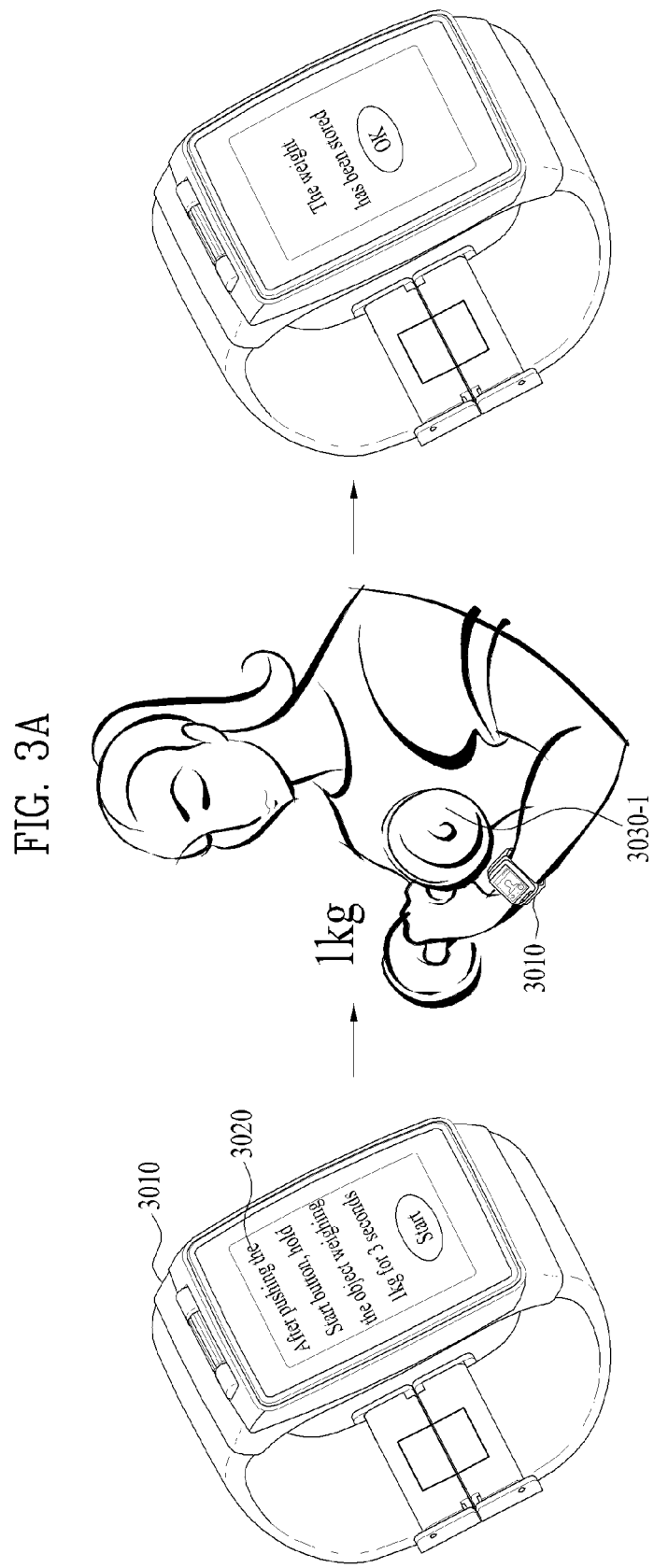

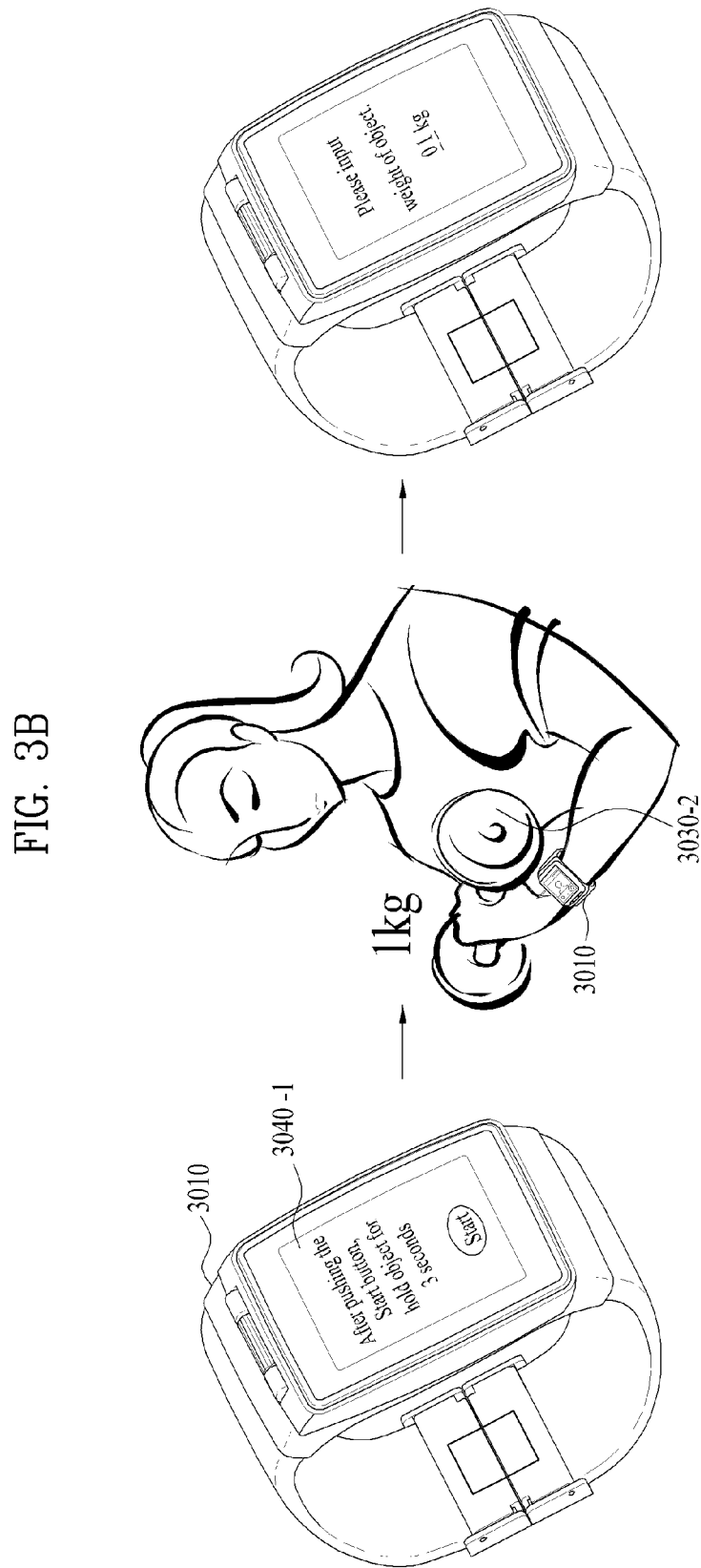

WEARABLE DEVICE AND METHOD FOR CONTROLLING THE SAME

This application claims the benefit of the Korean Patent Application No. 10-2013-0145079, filed on Nov. 27, 2013, which is hereby incorporated by reference as if fully set forth herein.

BACKGROUND OF THE INVENTION

Field of the Invention

The present specification relates to a wearable device. And, most particularly, the present specification relates to a wearable device that can generate reference data and measurement data and that can obtain a weight of an object that is to be measured (hereinafter referred to as a "measurement object") by comparing the two different data sets.

Discussion of the Related Art

With the technical evolution, research and development of wearable devices are being accelerated. Herein, a wearable device refers to a device that can be naturally and easily worn on a user's body, such as clothing or accessories, i.e., watches, glasses, rings, and so on. Since the wearable device is being worn on the user's body, bio-signals of the user may be detected by using diverse types of sensors. Accordingly, by detecting a bio-signal, which is generated by the user's motion of holding lifting a specific object, the wearable device may estimate the weight of the corresponding object.

However, since the bio-signal corresponds to a signal that is generated in accordance with the physical movements and physical characteristics of the user, the bio-signal may be differently detected with respect to each user even in the same situation. Accordingly, even in case multiple users are each holding an object having the same weight, the respective bio-signal may be detected differently. As a result, it may be disadvantageous in that the accuracy of the weight of the held object, which is estimated by using the bio-signal, may be degraded.

SUMMARY OF THE INVENTION

Accordingly, the present specification is directed to a wearable device and a method for controlling the same that substantially obviate one or more problems due to limitations and disadvantages of the related art.

An object of the present specification is to provide a wearable device and a method for controlling the same that can generate reference data with respect to each user as reference data that are compared with a bio-signal, which is generated in accordance with the user's motion of holding an object that is to be measured.

Another object of the present specification is to provide a wearable device and a method for controlling the same that can obtain the weight of the object that is to be measured by comparing and analyzing the measurement data and the reference data.

Yet another object of the present specification is to provide a wearable device and a method for controlling the same that can generate reference data respective to multiple reference objects, so as to update pre-stored reference data or to obtain the weight of the object that is to be measured.

Yet another object of the present specification is to provide a wearable device and a method for controlling the same that can generate user identification information for identifying a user, by using the measurement data and the reference data.

A further object of the present specification is to provide a wearable device and a method for controlling the same that can obtain user health information by generating data in accordance with a predetermined time interval and by comparing the differently generated data with one another.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a wearable device, comprising a bio-signal sensor unit configured to sense a bio-signal; a storage unit configured to store data; and a processor configured to control the bio-signal sensor unit and the storage unit, wherein the processor is further configured to: generate first reference data including a weight of a first reference object and a first bio-signal being generated by holding the first reference object when the first bio-signal is detected, generate measurement data including a second bio-signal being generated by holding a measurement object, when the second bio-signal is detected, and obtain a weight of the measurement object by comparing the measurement data with the first reference data.

It is to be understood that both the foregoing general description and the following detailed description of the present specification are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 3a and FIG. 3b illustrate a wearable device generating reference data according to an exemplary embodiment;

DETAILED DESCRIPTION OF THE INVENTION

Although the terms used in the present specification are selected from generally known and used terms, the terms used herein may be varied or modified in accordance with the intentions or practice of anyone skilled in the art, or along with the advent of a new technology. Alternatively, in some particular cases, some of the terms mentioned in the description of the present specification may be selected by the applicant at his or her discretion, the detailed meanings of which are described in relevant parts of the description herein. Furthermore, it is required that the present specification is understood, not simply by the actual terms used but by the meaning of each term lying within.

Reference will now be made in detail to the preferred embodiments of the present specification, examples of which are illustrated in the accompanying drawings. However, it should be understood that the present specification will not be limited only to the example presented in the description of the present specification set forth herein.

Figure 1:
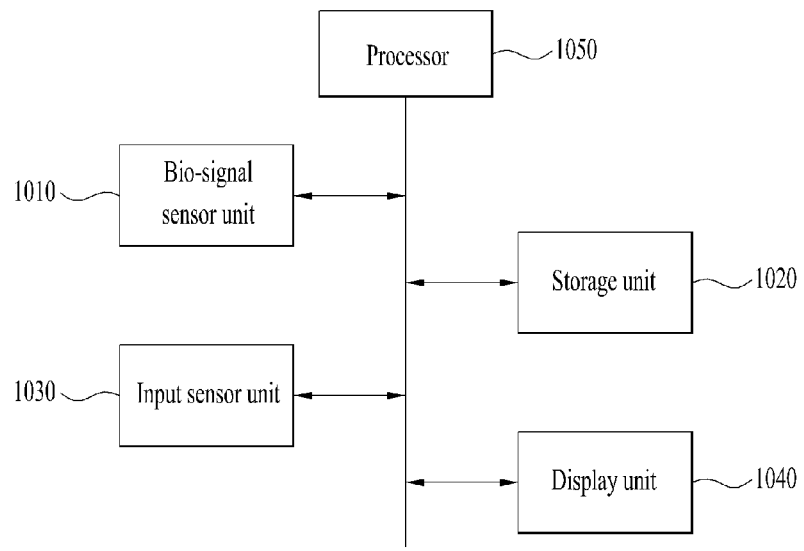
FIG. 1 illustrates a block view of a wearable device according to an exemplary embodiment.

FIG. 1 illustrates a block view of a wearable device according to an exemplary embodiment. Referring to FIG. 1, the wearable device may include a bio-signal sensor unit 1010, a storage unit 1020, an input sensor unit 1030, a display unit 1040, and a processor 1050.

The bio-signal sensor unit 1010 may sense diverse types of bio-signals. And, more specifically, the bio-signal sensor unit 1010 may sense diverse types of bio-signals of a user wearing the wearable device. Herein, a bio-signal may refer to diverse types of biological signals generated by the user's physical or bodily movements, which may be sensed through the user's body. According to an exemplary embodiment, the bio-signal sensor unit 1010 is worn on or attached to the user's body, so as to be capable of sensing at least one of muscular contraction level, electromyogram, skin conductivity, brainwave, pulse rate, respiration volume, electrocardiogram, blood pressure, blood flow rate, and heart rate as a bio-signal.

The bio-signal sensor unit 1010 may use at least one sensing means, which is equipped in the wearable device, so as to sense the bio-signal of the user. According to the exemplary embodiment, at least one of the sensing means may include a muscular tension sensor, electromyogram sensor, muscle strength sensor, skin conductivity sensor, brainwave sensor, electrocardiogram sensor, respiration sensor, blood pressure sensor, blood flow rate sensor, body temperature measurement sensor, heart rate sensor, gravity sensor, acceleration sensor, body temperature conduction sensor, and so on. The above-described sensors may each be included in the wearable device as a separate element, or the above-described sensors may be integrated as a single element, thereby being included in the wearable device. The bio-signal sensor unit 1010 may use at least one of the above-described sensors so as to sense the bio-signal and may then transmit the sensed result to the processor 1050.

The storage unit 1020 may store diverse forms of data either temporarily or permanently. For example, the storage unit 1020 may store diverse types of data related to audio, video, applications, images, information, and so on. Additionally, the storage unit 1020 may store data, which are generated in accordance with the sensed result sensed through the at least one sensor equipped in the wearable device. At this point, when data are generated, the storage unit 1020 may temporarily or permanently store the generated data without any separate storage command from the processor 1050.

Moreover, the storage unit 1020 may temporarily store data received from an external source through a communication unit. At this point, the storage unit 1020 may be used to perform buffering in order to output the data received from an external source to the wearable device. Meanwhile, in the present specification, the storage unit 1020 represents diverse types of digital data storage space, such as flash memory, Random Access Memory (RAM), Solid State Drive (SSD), and so on.

The input sensor unit 1030 may sense any input toward the wearable device. More specifically, the input sensor unit 1030 may use at least one of the sensing means equipped in the wearable device, so as to sense any input toward the wearable device. According to the exemplary embodiment, the at least one of the sensing means may include diverse sensing means, such as a gravity sensor, a motion sensor, a gesture sensor, a close-range sensor, an infrared light ray sensor, a camera sensor, a touch sensor, a voice recognition sensor, and a pressure sensor. The above-described sensors may each be included in the wearable device as a separate element, or the above-described sensors may be integrated as a single element, thereby being included in the wearable device. The input sensor unit 1040 may sense the input toward the wearable device by using at least one of the above-described sensors, and, then, the input sensor unit 1040 may transmit the sensed result to the processor 1050.

The display unit 1040 may output an image of a display screen. In other words, the display unit 1040 may display an image of the display screen. Herein, an image may represent visual information that can be visually recognized by the user. And, herein, an image may include diverse types of photos, drawings, moving pictures, texts, user interfaces, and so on. The display unit 1040 may display diverse types of images based upon a control command of the processor 1050.

The processor 1050 may process diverse data existing in the wearable device, thereby being capable of executing diverse applications. Additionally, the processor 1050 may execute diverse commands based upon any received input. Furthermore, the processor 1050 may control each of the above-described units of the wearable device and may control data transmission/reception between each unit.

Most particularly, the present specification relates to a wearable device that can detect a bio-signal so as to obtain a weight of an object. Accordingly, the processor 1050 may detect a bio-signal by using the bio-signal sensing unit 1010 and may then generate data including the detected bio-signal. For example, as the user is holding (or lifting) a specific object, the processor 1050 may detect a bio-signal, which is generated with respect to the user's holding (or lifting) of the object, thereby generating data including the detected bio-signal. Herein, a bio-signal that is generated by a muscle used only when the user is holding an object, or brainwaves that are generated only when the user is holding an object may be represented as the bio-signal that is generated with respect to the user's holding of the object. Alternatively, the processor 1050 may provide a user interface for generating the above-described data. And, a detailed description of the same will be provided later on with reference to FIG. 3a to FIG. 3c.

Thereafter, by comparing the data, which are generated as described above, with other data, the processor 1050 may obtain a weight (or weight information) of the specific object he (or she) is holding. And, this will be described in more detail later on with reference to FIG. 3a to FIG. 3c.

Meanwhile, the processor 1050 may provide diverse user interface so as to generate the data. This will be described in more detail later on with reference to FIG. 3a to FIG. 3c. Moreover, the processor 1050 may also generate health information of the user and user identification information by comparing each set of the data, which are generated as described above, with one another. This procedure will be described in more detail later on with reference to FIG. 6 and FIG. 7.

Although it is not shown in the drawing, the wearable device may be optionally equipped with a communication unit and/or a power unit.

The communication unit (not shown) may use diverse protocols so as to perform communication with an external device and/or a web server, thereby being capable of transmitting/receiving data. At this point, the communication unit may access a network via wired or wireless communication, so as to transmit/receive data.

The power unit (not shown) corresponds to a power source being connected to a battery, which is provided inside the wearable device, or to an external power, so as to supply power to the wearable device.

Hereinafter, in case each process step or operation, which is performed by the wearable device, is initiated or proceeded by the sensing of an input, it will be apparent that the description of the process of generating a signal with respect to a sensed input and receiving the generated signal is included in the above-described procedure, and, therefore, a repeated description of the same is not required to be provided. Additionally, it may be expressed herein that, in accordance with a received input, the processor 1050 controls the wearable device or at least one unit included in the wearable device. And, therefore, the processor 1050 may be regarded as the wearable device itself and may be described accordingly.

Meanwhile, in the block view of the wearable device according to the exemplary embodiment shown in FIG. 1, each of the blocks respectively represents elements of the wearable device that are logically differentiated. Accordingly, the elements of the above-described wearable device may be mounted as a single chip or a plurality of chips based on the design of the wearable device.

Figure 2:
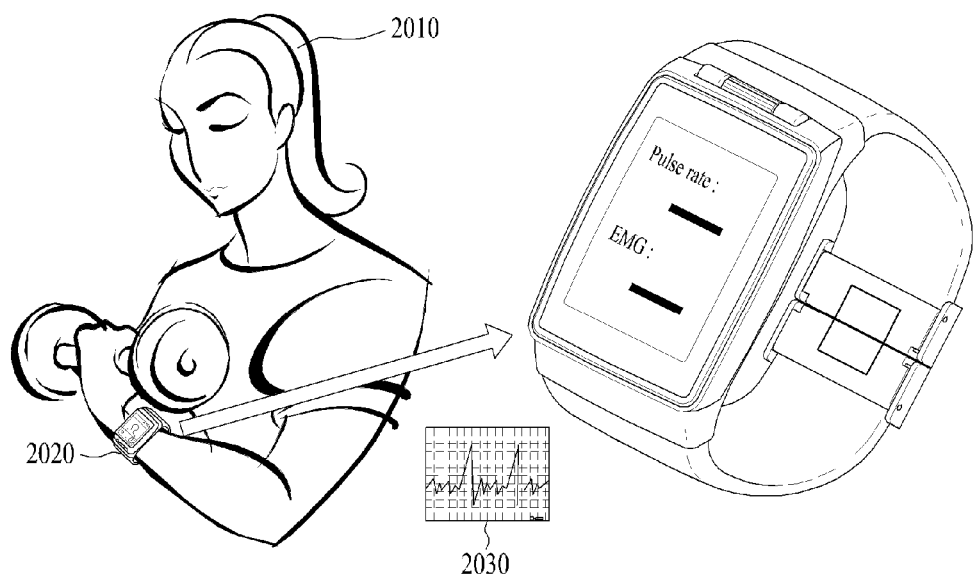
FIG. 2 illustrates a wearable device detecting a bio-signal according to an exemplary embodiment.

FIG. 2 illustrates a wearable device detecting a bio-signal according to an exemplary embodiment. The present specification will be described based upon a smart watch as a main embodiment of the wearable device 2020 for simplicity in the description.

The wearable device 2020 may detect a bio-signal 2030 by using a bio-signal sensor unit. Most particularly, the present specification relates to a wearable device 2020 that can indirectly obtain the weight of an object held by the user by detecting a bio-signal 2030 of the user 2010, which is generated as the user 2010 is holding the corresponding object. Accordingly, among the many signals that may be generated due to the physical movement of the user 2010, the wearable device 2020 of the present specification may mostly detect a bio-signal 2030, which is be generated or changed in accordance with the user's motion of holding the object. Meanwhile, in the present specification, the measurement object is a weight measuring target. In other words, the measurement object indicates a target object to be measured so as to obtain its weight.

According to an exemplary embodiment, the wearable device 2020 may detect a pulse (or pulse rate) of the user 2010. This is because the pulse rate of the user 2010 may vary in accordance with the weight of the object, which the user 2010 is holding. For example, the pulse rate of the user 2010 may become faster when the user 2010 is holding a heavy object as compared to when the user 2010 is holding a relatively lighter object. The wearable device 2020 may detect the pulse of the user 2010 by detecting a periodic vibration, which is sensed from the user's wrist. In this case, the wearable device 2020 may correspond to a smart watch, which is worn on the wrist of the user 2010, and the bio-signal sensor unit may be located on a band portion and/or rear side surface of the smart watch, so as to sense the pulse rate of the user 2010. When the wearable device 2020 detects such pulse rate of the user 2010, the wearable device 2020 may be capable of generating data including the detected pulse rate.

According to another exemplary embodiment, the wearable device 2020 may detect an electromyogram of the user 2010. Herein, the electromyogram (EMG) may represent an electrical signal, which is generated along muscle tissues from the surface of the muscle in accordance with the user's physical movement. Since the EMG is detected through the skin of the user 2010, any wearable device that can be worn while being in contact with the surface of the user's skin may be used as the wearable device according to the exemplary embodiment without limitation. Since the wearable device 2020 is capable of interpreting the intentions or movements of the user 2010 through the detected electromyogram, the wearable device 2020 may detect the user's EMG as a bio-signal 2030 for interpreting the dynamic physical activity of the user 2010. When the wearable device 2020 detects such EMG of the user 2010, the wearable device 2020 may be capable of generating data including the detected EMG.

Moreover, the wearable device 2020 may also detect at least one of muscular contraction level, skin conductivity, brainwave, pulse rate, electrocardiogram, respiration volume, blood pressure, blood flow rate, body temperature, and heart rate as the bio-signal. Herein, however, in case a single bio-signal 2030 is independently detected, the accuracy in interpreting the physical activity of the user 2010 may be degraded. Therefore, the wearable device 2020 may detect the bio-signal 2030 as a combination of the examples mentioned above. For example, the wearable device 2020 may simultaneously detect the EMG and the brainwave as the bio-signal 2030 of the user 2010, thereby generating data including the detected EMG and brainwave.

Figure 3C:
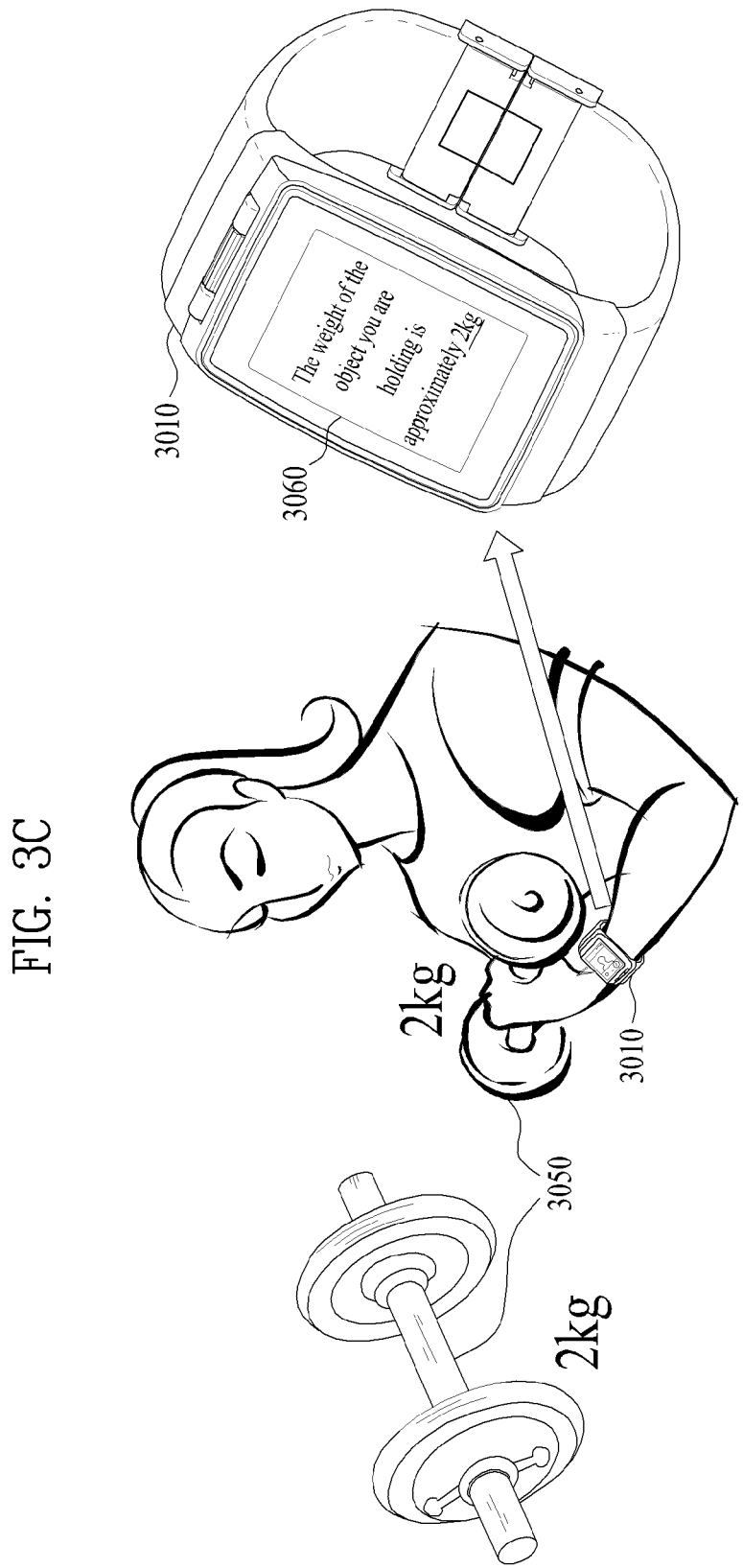
FIG. 3c illustrates a wearable device obtaining a weight of a measurement object by using reference data according to an exemplary embodiment.

FIG. 3a to FIG. 3c illustrate a wearable device obtaining the weight of a measurement object by detecting a bio-signal of the user according to an exemplary embodiment. More specifically, FIG. 3a and FIG. 3b illustrate a wearable device 3010 generating reference data by detecting a bio-signal respective to a reference object according to the exemplary embodiment. Additionally, FIG. 3c illustrates the wearable device 3010 obtaining the weight of the object that is to be measured (hereinafter referred to as a "measurement object") by using the generated reference data according to the exemplary embodiment. Herein, each drawing will be differentiated and described accordingly for simplicity in the description. The wearable device 3010 according to the exemplary embodiment may be operated by the order of FIG. 3a to FIG. 3c. Meanwhile, in the present specification, the reference object represents an object that is targeted to have its weight compared with the measurement object in order to obtain the weight of the measurement object. Furthermore, in the present specification, reference data represents data including the weight of the reference object and the bio-signal generated in accordance with the user's motion of holding the reference object.

In order to obtain the weight of the measurement object, the wearable device 3010 may first generate reference data respective to the reference object, which is a weight comparison target with a measurement object. More specifically, the wearable device 3010 may detect a bio-signal, which is generated in accordance with the user's motion of holding the reference object, and may then generate reference data including the detected bio-signal and weight information of the reference object. By detecting a unique bio-signal, which is generated in accordance with the user's motion of holding an object, or by providing a user interface for generating reference data, the wearable device 3010 may generate reference data. This may be identically applied to a case when the wearable device generates measurement data.

Meanwhile, in addition to the bio-signal and the weight, the wearable device 3010 may also generate reference data by adding content related to at least one of reference object type, the user holding the reference object, and at least one of date, time, interval, and place at which the reference data is generated. This may be identically applied to a case when the wearable device generates measurement data.

The wearable device 3010 may generate reference data respective to each user. This is because the bio-signal, which corresponds to a signal being generated in accordance with the physical movements of the user, may be differently detected for the same activity due to the different bodily structure and physical features of each user. More specifically, even if the detected physical movement is the same, the bio-signal may be differently detected with respect to the bodily structure and physical features of each user, such as level of muscular development, number of muscular tissues, thickness of the skin, bone density, gender, physical quotient, and so on. For example, in case a man and a woman both having the same physical quotient (PQ) are holding the same object in the same holding position, the bio-signal detected from each user may differ from one another. This is because, in addition to the physical quotient (PQ), a man and a woman may have different bodily structures, such as muscular development level, number of muscular tissues, thickness of the user's skin, and so on.

Therefore, the wearable device 3010 of the present specification is required to generate reference data for each user, wherein the reference data function as a reference standard for comparing the detected bio-signals. More specifically, with respect to each user, the wearable device 3010 may generate reference data respective to the bio-signal and weight, which are detected when the user holds a reference object, and may then use the generated reference data for obtaining information on the weight of the measurement object. A method for obtaining information on the weight of the measurement object by using the reference data will be described in more detail later on with reference to FIG. 3c.

Hereinafter, diverse exemplary embodiments of the wearable device 3010, which generates the above-described reference data, will be described in detail.

FIG. 3a illustrates a wearable device 3010 generating reference data according to an exemplary embodiment.

According to the exemplary embodiment, the wearable device 3010 may generate reference data by using a bio-signal, which is generated when the user is holding an object 3030-1 having a predetermined weight. More specifically, the wearable device 3010 may detect a bio-signal, which is generated when the user is holding an object 3030-1 having a predetermined weight, and may then generate reference data including the detected bio-signal and the predetermined weight. At this point, the wearable device 3010 may provide a user interface 3020 for generating reference data. By using the user interface 3020, the wearable device 3010 guides the user to hold the object 3030-1 having the predetermined weight. Thereafter, the wearable device 3010 may generate reference data by storing the bio-signal that is generated when the user holds the object 3030-1 having the predetermined weight.

For example, as shown in the drawing, the user interface 3020 may provide a guidance message, such as "After pushing the Start button, hold the object of 1 kg for 3 seconds." At this point, in accordance with the guidance provided by the user interface 3020, after pushing the Start button, the user may hold the object 3030-1 having the predetermined weight, i.e., the object 3030-1 having the weight of 1 kg, for 3 seconds. In case the wearable device 3010 detects the user input respective to the "Start" button, the wearable device 3010 may store a bio-signal that is being detected for 3 seconds starting from the point when the user input of pushing the "Start" button has been detected. At this point, the wearable device 3010 may convert the detected bio-signal to a graph and store the converted graph.

The wearable device 3010 may generate the stored bio-signal and predetermined weight in the form of reference data. At this point, in order to differentiate the reference data generated with respect to each user, the wearable device 3010 may also generate information on the users (or user information) respective to the different sets of reference data as the reference data. Meanwhile, user identification information may be generated by using the reference data, which are generated with respect to each user. And, this will be described in more detail later on with reference to FIG. 6.

FIG. 3b illustrates a wearable device 3010 generating reference data according to an exemplary embodiment.

According to the exemplary embodiment, in case the user is holding an object 3030-2 having an arbitrary weight, the wearable device 3010 may generate reference data by using a bio-signal, which is generated with respect to such user action. At this point, the wearable device 3010 may directly receive an input on the weight of the object 3030-2 from the user and may then generate reference data. As described above with reference to FIG. 3a, in this exemplary embodiment, the wearable device 3010 may provide a user interface 3040-1 and 3040-2 for generating reference data. By using the corresponding user interface 3040-1 and 3040-2, the wearable device 3010 guides the user to hold the object 3030-2 having the arbitrary weight. Thereafter, the wearable device 3010 may generate reference data by storing both the bio-signal, which is generated when the user holds the object 3030-2, and the weight of the object 3030-2, which is inputted by the user.

For example, as shown in the drawing, the corresponding user interface 3040-1 may provide a guidance message, such as "After pushing the Start button, hold the object for 3 seconds." At this point, in accordance with the guidance provided by the user interface 3040-1, after pushing the Start button, the user may hold the object 3030-2 having the arbitrary weight for 3 seconds. In case the wearable device 3010 detects the user input respective to the "Start" button, the wearable device 3010 may store a bio-signal that is being detected for 3 seconds starting from the point when the user input of pushing the "Start" button has been detected. At this point, the wearable device 3010 may convert the detected bio-signal to a graph and store the converted graph.

Furthermore, the corresponding user interface 3040-2 may provide a weight input window configured to receive an input of the weight of the object 3030-2 held by the user. The user may directly input the weight of the object 3030-2 he (or she) is holding through the weight input window. Accordingly, the wearable device 3010 may generate the stored bio-signal and the weight received from the user as the reference data. At this point, in order to differentiate the reference data generated with respect to each user, the wearable device 3010 may also generate user information corresponding to each reference data as the reference data.

Moreover, the wearable device 3010 may generate the reference data by using diverse methods. And, such methods will not be limited only to the above-described exemplary embodiments. Furthermore, the user interface, which is provided in order to generate the reference data, may also be realized according to diverse exemplary embodiments. And, the user interface will not be limited only to the above-described exemplary embodiments. Hereinafter, a wearable device 3010 that can obtain the weight of an measurement object by using the generated reference data will be described in detail.

FIG. 3c illustrates a wearable device obtaining a weight of a measurement object by using reference data according to an exemplary embodiment.

The wearable device 3010 may obtain the weight of a measurement object 3050 by using the reference data. More specifically, the wearable device 3010 may generate measurement data related to the measurement object 3050. Then, by comparing the measurement data with the reference data, the wearable device 3010 may obtain the weight of the measurement object 3050. Herein, the measurement data may represent data included the bio-signal, which is generated in accordance with the user's action of holding the measurement object 3050. The wearable device 3010 may detect the bio-signal, which is generated in accordance with the user's action of holding the measurement object 3050, and may then generate the measurement data including the detected bio-signal.

At this point, the wearable device 3010 may provide a user interface for generating measurement data (not shown). As described above with reference to FIG. 3a and FIG. 3b, after detecting a user input through the corresponding user interface, the wearable device 3010 may generate measurement data by using the bio-signal, which is detected for a predetermined period of time. For example, the corresponding user interface may provide a guidance message, such as "After pushing the Start button, hold the object you wish to weigh for 3 seconds." At this point, the wearable device 3010 may detect the user input respective to the guidance message and may then store the bio-signal, which has been detected for 3 seconds starting from the detection point of the user input. Thus, the wearable device 3010 may generate the measurement data. The detailed description of the above is the same as the description of the user interface, which is given with reference to FIG. 3a and FIG. 3b. However, the user interface that is being provided in order to generate the measurement data will not be limited only to the exemplary embodiment described herein. And, therefore, diverse variations may be realized without departing from the scope allowed by anyone skilled in the art.

As described above, when the reference data and measurement data are generated, the wearable device 3010 may compare the two different types of data. More specifically, the wearable device 3010 may compare the bio-signal, which is included in the reference data, with the bio-signal, which is included in the measurement data, thereby being capable obtaining the relative weight of the measurement object 3050 with respect to the reference object 3050. For example, the wearable device 3010 may calibrate the bio-signal included in the reference data. And then, by applying the calibrated result to the bio-signal being included in the measurement data, the wearable device 3010 may obtain the relative weight of the measurement object 3050 with respect to the reference object 3050. This will be described in more detail later on with reference to FIG. 4a and FIG. 4b.

Meanwhile, in case the wearable device 3010 has obtained the weight of the measurement object 3050, the wearable device 3010 may display the obtained weight on a display unit 3060.

Figure 4A:
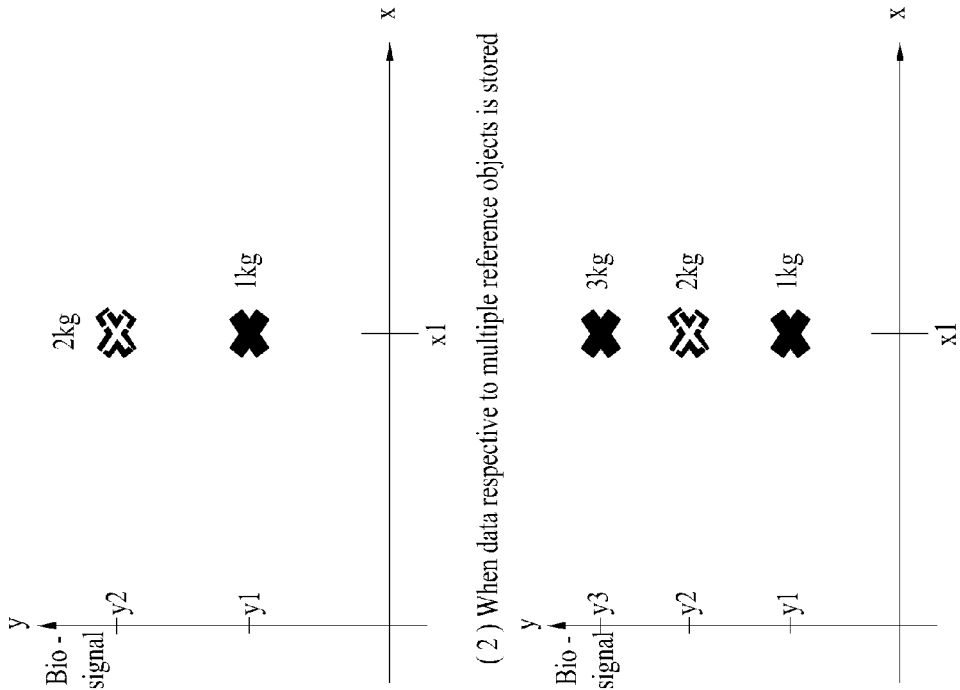
FIG. 4a and FIG. 4b illustrate a wearable device obtaining a weight of a measurement object by comparing reference data to measurement data according to an exemplary embodiment.

FIG. 4a illustrates a wearable device obtaining a weight of a measurement object by comparing reference data to measurement data according to an exemplary embodiment.

According to the exemplary embodiment, the wearable device 4010 may generate data by detecting a bio-signal, which is generated in a situation when the object 4020 is held and when the position of the held object 4020 is stationary. In other words, when the user is holding the object 4020, the wearable device 4010 may generate the data by detecting a bio-signal, which is generated in a situation when the position of the held object 4020 remains unchanged for a predetermined period of time. For example, when the user holds the object 4020 in the grip of his (or her) hand, the wearable device 4010 may generate data by detecting the bio-signal, which is generated in a situation when the user does not move his (or her) hand for a predetermined period of time. However, in the present specification, the stationary position of the object 4020 indicates that the corresponding object 4020 is "substantially" fixed. And, therefore, even if the position of the held object 4020 changes within a predetermined range of movement, the corresponding object 4020 may be regarded as being in a stationary state.

At this point, the wearable device 4010 may detect the generated bio-signal and may then convert the detected bio-signal to a graph, thereby generating data. Most particularly, as shown in the drawing, in order to ensure convenience in the comparison and reliability of the compared result, the wearable device 4010 may convert the bio-signal to a two-dimensional (2D) graph and may then generate data including the converted graph. Accordingly, by converting the bio-signal respective to the reference object to a graph, the wearable device 4010 may generate reference data. And, by converting the bio-signal respective to the measurement object 4020 to a graph, the wearable device 4010 may generate measurement data. However, this will not be limited only to the above-described exemplary embodiment. And, therefore, the wearable device 4010 may generate data respective to the corresponding bio-signal without having to convert the bio-signal to a graph. Moreover, even in case the bio-signal is converted to a graph, the form of the converted graph will not be limited to the above-described exemplary embodiment. And, therefore, diverse forms of graphs may exist.

As shown in the drawing, the bio-signal being generated in a situation when the position of the object 4020 is stationary may be indicated in a non-continuous format. At this point, the x-axis may represent time or position, and the y-axis may represent the size or intensity of the detected bio-signal.

The wearable device 4010 may compare the bio-signals that are respectively converted to graphs with one another, so as to obtain the weight of the measurement object 4020. More specifically, the wearable device 4010 may obtain the weight of the measurement object 4020 by comparing y values at the same specific point in the x-axis. For example, at point x1, the bio-signal graph corresponding to the reference object has a value of y1. And, at the same point x1, if the bio-signal graph corresponding to the measurement object 4020 has the value of y2, by comparing the y1 value and the y2 value with one another, the wearable device 4010 may gain the weight of the measurement object 4020. More specifically, by calculating a ratio of the y2 value with respect to the y1 value through a consistent operation, the wearable device 4010 may obtain the weight of the measurement object 4020. For example, when the y2 value is twice the value of the y1 value, by multiplying the weight of the reference object, which is pre-stored in the reference data, by 2, the wearable device 4010 may obtain the weight of the measurement object 4020.

Based upon the above-described characteristics, the description provided above may be identically applied even to a case when multiple sets of reference data respective to multiple reference objects are stored. Therefore, by comparing the different y values respective to the same x value with one another, the wearable device 4010 may obtain the weight of the measurement object 4020. However, in this case, since a larger amount of reference data is being used, the weight of the measurement object 4020 may be more accurately obtained as compared to when obtaining the weight of the measurement object 4020 by using only one set of reference data.

Figure 4B:
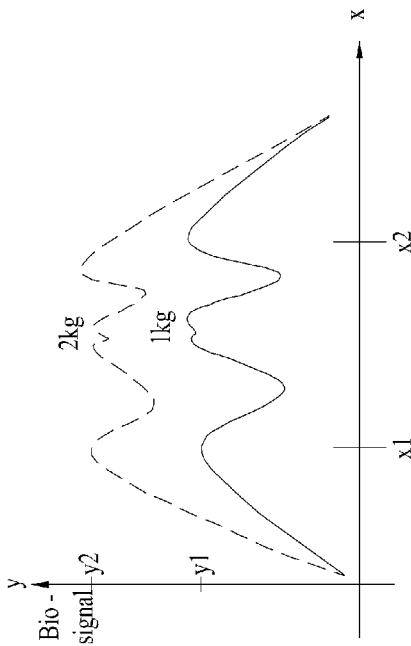
Figure 4B:
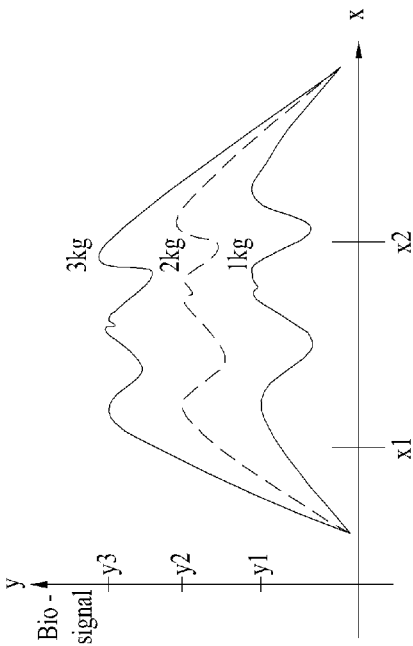
Figure 4B:
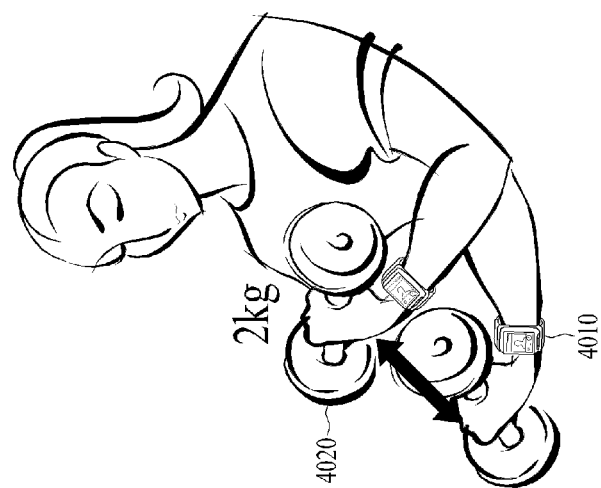

FIG. 4b illustrates a wearable device obtaining a weight of a measurement object by comparing reference data with measurement data according to an exemplary embodiment. Referring to this drawing, portions of the detailed description that are identical to the description, which is provided above with reference to FIG. 4a, will be, omitted.

According to the exemplary embodiment, after the object 4020 is held by the user, the wearable device 4010 may generate data by detecting a bio-signal, which is generated in a situation when the position of the held object is mobile. In other words, after the object is held by the user, the wearable device 4010 may generate data by detecting a bio-signal, which is generated in a situation when the position of the held object is not stationary. For example, when the user holds the object in the grip of his (or her) hand, the wearable device 4010 may detect the bio-signal, which is generated in a situation when the user moves his (or her) hand up and down, so as to generate data. However, in the present specification, the mobile position of the object indicates that the corresponding object is "substantially" mobile. And, therefore, if the position of the held object deviates from a predetermined range of movement, the corresponding object may be regarded as being in a mobile state.

At this point, the wearable device 4010 may generate data by detecting the generated bio-signal and by converting the detected bio-signal to a graph. However, this will not be limited only to the above-described exemplary embodiment. Therefore, as described above, the wearable device 4010 may generate data respective to the bio-signal without converting the bio-signal to a graph.

As shown in the drawing, the bio-signal which is generated in a situation when the position of the object 4020 is mobile may be indicated in a continuous format. At this point, the x-axis may represent time or position, and the y-axis may represent the size or intensity of the detected bio-signal.

The wearable device 4010 may compare the bio-signals that are respectively converted to graphs with one another, so as to obtain the weight of the measurement object 4020. According to the exemplary embodiment, the wearable device 4010 may obtain the weight of the measurement object 4020 by comparing y values at the same specific point in the x-axis. The detail description of the same is identical to that of FIG. 4a.

According to another exemplary embodiment, the wearable device 4010 may calculate an average value of the y values existing within a constant range of each bio-signal graph. Thereafter, by comparing the calculated average values with one another, the wearable device 4010 may obtain the weight of the measurement object 4020. For example, the wearable device 4010 may calculate the average value of y values corresponding to sections x1 to x2 from each bio-signal graph. Subsequently, by comparing the average values, which are calculated from each bio-signal graph, with one another, the wearable device 4010 may obtain the weight of the measurement object 4020.

Additionally, the description provided above may be identically applied to a case when multiple sets of reference data respective to multiple reference objects are stored. However, in this case, since a larger amount of reference data is being used, the weight of the measurement object 4020 may be more accurately obtained as compared to when obtaining the weight of the measurement object 4020 by using only one set of reference data.

Moreover, by interpreting bio-signals using diverse graph interpretation methods and calculation methods, the wearable device 4010 may be capable of obtaining information that is useful to the user. For example, by interpreting the bio-signal graph, the wearable device 4010 may detect a number of times the user has lifted the measurement object 4020 or the reference object. More specifically, by counting a number of peak points of the graph within a predetermined range of x of the corresponding bio-signal graph, the wearable device 4010 may obtain the number of times the object has been lifted.

Figure 5:
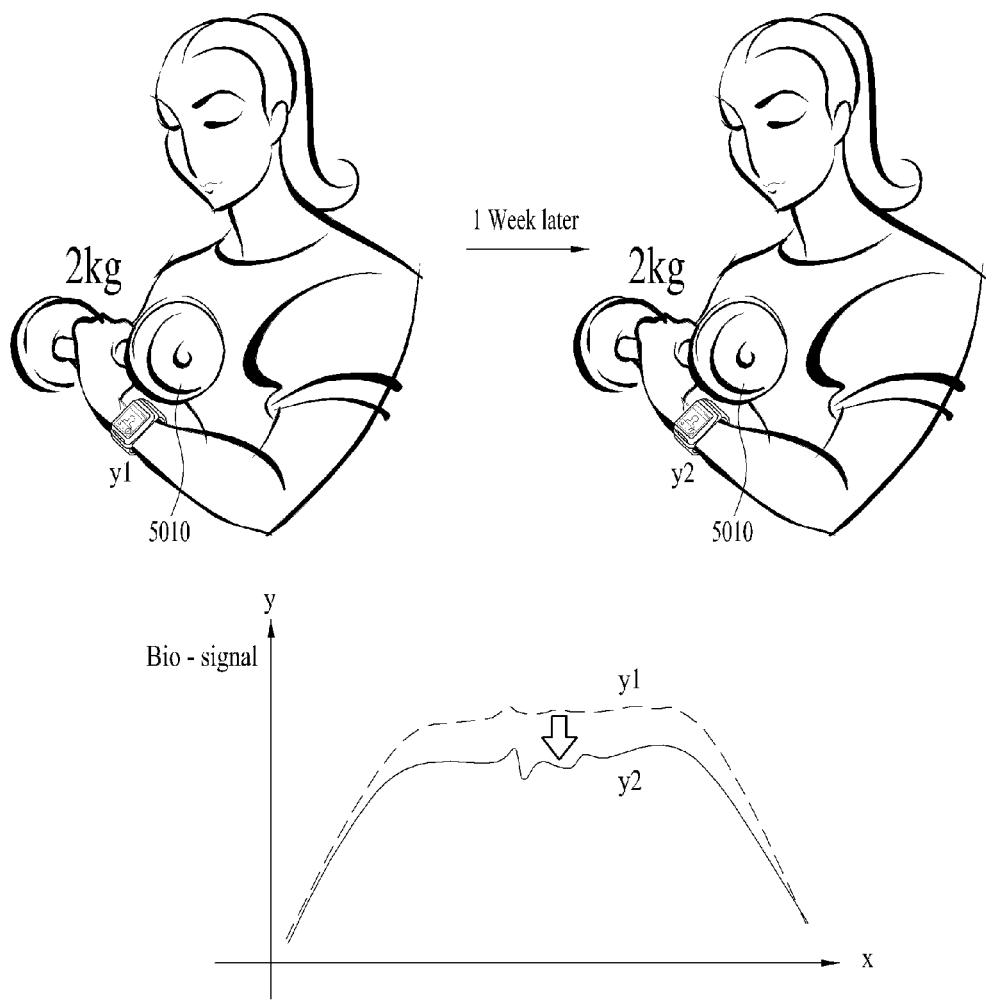
FIG. 5 illustrates a wearable device generating new reference data according to an exemplary embodiment.

FIG. 5 illustrates a wearable device generating new reference data according to an exemplary embodiment.

Since the physical condition of a human being is constantly changing, in case of obtaining the weight of a measurement object by using reference data, which have been generated a predetermined period of time earlier, the accuracy of the obtained weight may be degraded. Therefore, the wearable device according to the exemplary embodiment may update the pre-stored reference data by generating new reference data and by using the newly generated reference data. In this exemplary embodiment, the pre-stored reference data will hereinafter be referred to as first reference data, and the newly generated reference data will hereinafter be referred to as second reference data for simplicity in the description.

More specifically, the wearable device may generate the second reference data after generating the first reference data. At this point, the wearable device may provide a user interface for generating the second reference data, and detailed description of the same corresponds to the detailed description given above with reference to FIG. 3a and FIG. 3b.

The second reference data may correspond to data respective to a reference object 5010 having the same weight as the first reference data, or the second reference data may correspond to data respective to a reference object having a different weight. In case the second reference data correspond to the data respective to the reference object 5010 having the same weight as the first reference data, the wearable device may use the second reference data, so as to update the first reference data. Conversely, in case the second reference data correspond to data respective to the reference object having a weight being different from that of the first reference data, the wearable device may use the second reference data, so as to update the first reference data, or the wearable device may additionally store the second reference data along with the first reference data.

The wearable device may generate the second reference data if a predetermined period of time has passed since the generation of the first reference data. Herein, the predetermined period of time may be diversely varied in accordance with a physical change rate of the user, a change in the user's surrounding environment, the user's work-out cycle period, the user's work-out type, or an update cycle period directly set up by the user.

The wearable device may update the first reference data by using the weight obtaining result regarding the measurement object. More specifically, in case the wearable device has obtained the weight of the measurement object, the wearable device may use the measurement data and the obtained weight, so as to update the first reference data. Additionally, the wearable device may additionally store the measurement data reflecting the weight obtaining result along with the first reference data. Such measurement data may be used for obtaining a weight of a new measurement object.

Meanwhile, in case the second reference data is generated with respect to a reference object 5010 having the same weight as the first reference data, by comparing the first reference data and the second reference data with one another, the wearable device may obtain health information of the user. By comparing bio-signals (y1 and y2), which have been sequentially detected at constant time intervals, with one another, the wearable device may be capable of detecting physical changes of the user. By comparing and analyzing the bio-signals (y1 and y2), which are included in each set of reference data, the wearable device may be capable of detecting diverse change levels, such as an amount of muscles of the user, an amount of change in the user's body fat, a level of fatigue in the user's muscles, and so on. The wearable device may also generate health information including the detected physical change in the user's body, the analyzed result and the compared result. The user may be provided with diverse types of information related to the physical condition of the user through the health information.

Figure 6:
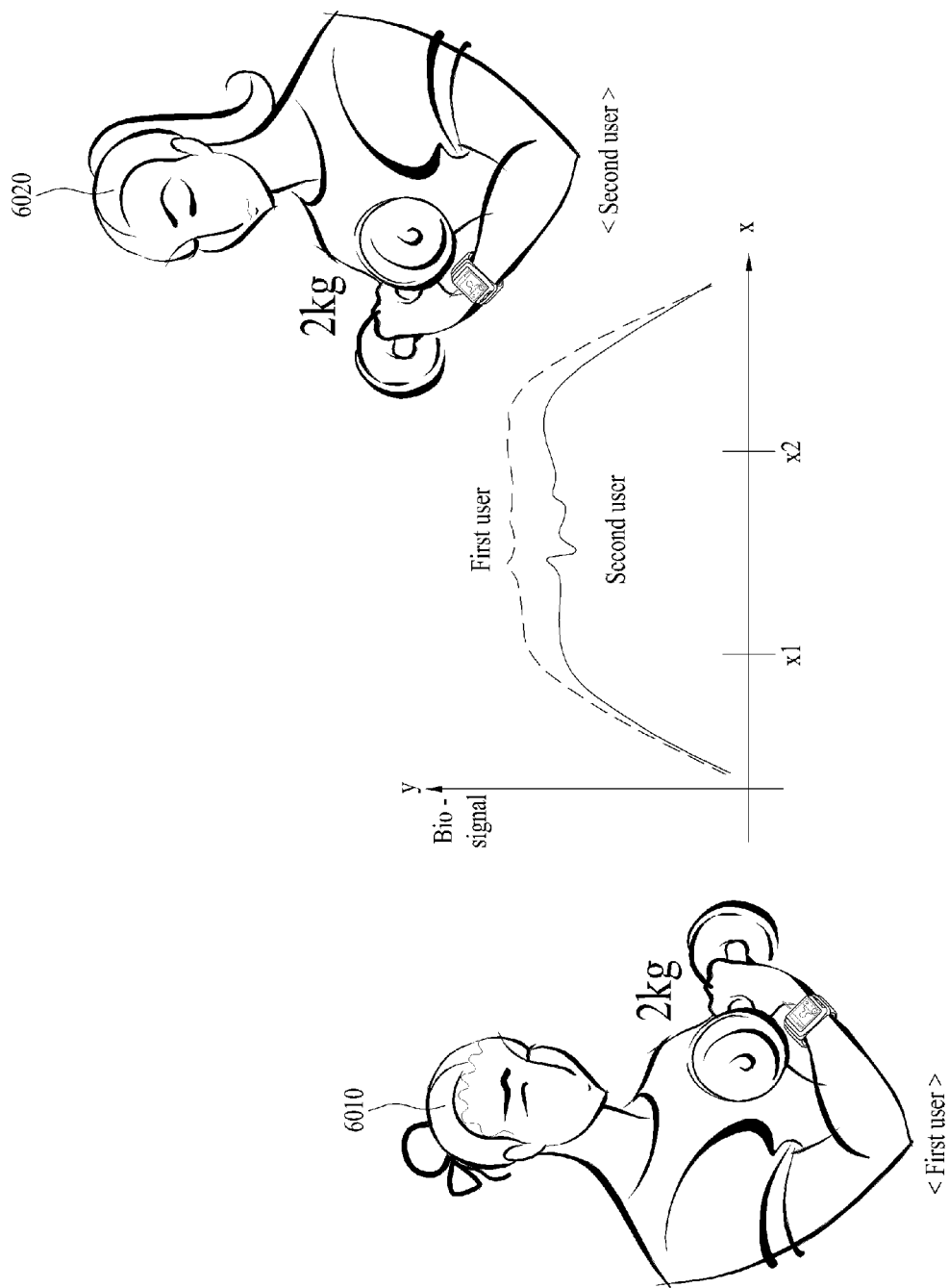
FIG. 6 illustrates a wearable device generating user identification information according to an exemplary embodiment.

FIG. 6 illustrates a wearable device generating user identification information according to an exemplary embodiment.

As described above, a bio-signal corresponds to a signal being generated by the physical movements of a user, and therefore, such bio-signal may be different from one another with respect to each user 6010 and 6020. In other words, just as fingerprints or pupils of a human being, the bio-signals may also be detected in different forms with respect to each user 6010 and 6020. Therefore, even when multiple users 6010 and 6020 are holding the same object, the detected bio-signal may be different from one another. The wearable device according to the exemplary embodiment may use the bio-signal, which is detected in different forms with respect to each user 6010 and 6020, so as to generate user identification information for identifying each user 6010 and 6020.

More specifically, the wearable device may generate user identification information. The user identification information includes bio-signals, which are generated with respect to the motion performed by the user 6010 and 6020 of holding the corresponding object, and personal information respective to the user who is holding the object. At this point, the wearable device may use the pre-generated reference data and/or measurement data, so as to generate the user identification information. By comparing the newly detected bio-signal with the bio-signal, which is included in the user identification information, the wearable device may be capable of identifying the user wearing the wearable device.

At this point, the wearable device may variously use the generated user identification information. Most particularly, the wearable device may use the user identification information on contents, documents, pictures or images, and so on, which require security. For example, the wearable device may use the user identification information as unlock information for unlocking the locked state of the wearable device. The wearable device may compare the detected bio-signal with the bio-signal included in the user identification information, and, in case the bio-signals are matched over a predetermined range, the wearable device may be capable of identifying the user respective to the corresponding user identification information. Accordingly, by simply wearing the wearable device and holding a predetermined object, the user may unlock the locked state of the wearable device. Additionally, the wearable device may also use the user identification information as unlock information for unlocking the locked state of the wearable device, such as view locked document, view locked picture or image, view locked message, execute lock function, and so on.

Figure 7:
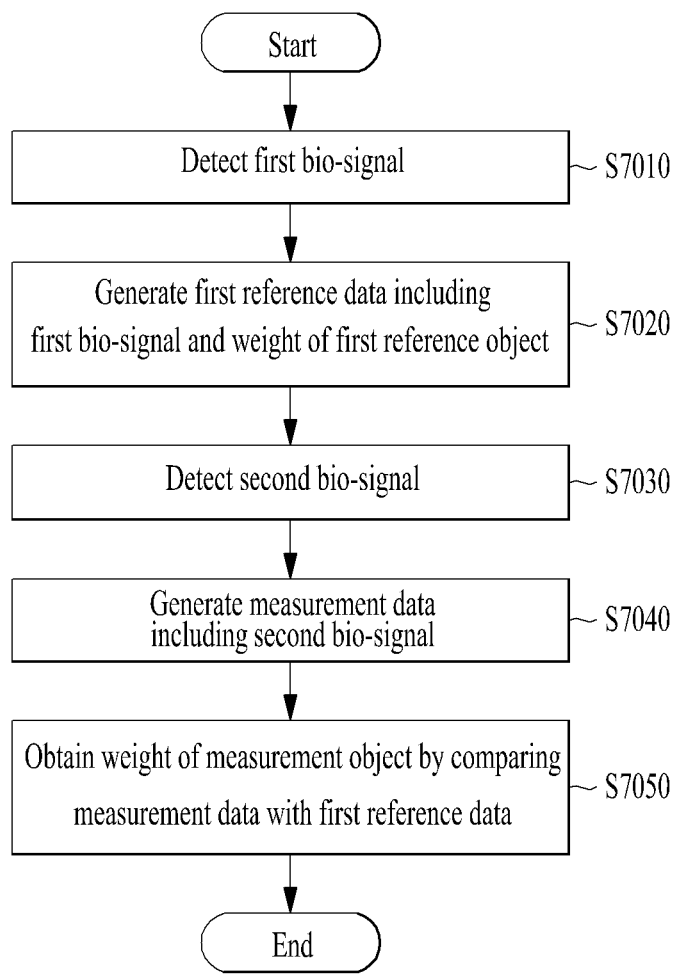
FIG. 7 illustrates a flow chart of a method for controlling a wearable device according to an exemplary embodiment.

FIG. 7 illustrates a flow chart of a method for controlling a wearable device according to an exemplary embodiment. In the flow chart shown herein, portions of the detailed description that are similar or identical to the detailed description given above with reference to FIG. 1 to FIG. 6 will be omitted for simplicity.

First of all, the wearable device may detect a first bio-signal (S7010). Herein, the first bio-signal may represent a bio-signal, which is generated in accordance with a motion of holding a first reference object.

Then, the wearable device may generate first reference data including the first bio-signal and a weight of the first reference object (S7020). At this point, the wearable device may provide a user interface for generating the first reference data. By having the user hold an object having a predetermined weight, or by having the user hold an object having an arbitrary weight, the first reference data may be generated. The detailed description of the same has already been provided above with reference to FIG. 3a and FIG. 3b.

Subsequently, the wearable device may detect a second bio-signal (S7030). Herein, the second bio-signal may represent a bio-signal, which is generated in accordance with a motion of holding a measurement object.

Thereafter, the wearable device may generate measurement data including the second bio-signal (S7040). The wearable device may provide a user interface for generating measurement data, and the detailed description of the same has already been provided above with reference to FIG. 3c. Meanwhile, although it is not shown in the flow chart, in case the wearable device generates the first reference data and the measurement data, the wearable device may convert the detected bio-signal to a graph and may then generate data including the converted bio-signal graph. This process is performed in order to facilitate the process of comparing each set of data with one another, and the detailed description of the same has already been provided above with reference to FIG. 4a and FIG. 4b.

Afterwards, the wearable device may compare the generated measurement data with the first reference data, so as to obtain the weight of the measurement object (S7050). In case the bio-signal is converted to a graph and included in each set of data, the wearable device may compare the bio-signal graph included in each data set with one another, so as to obtain the weight of the measurement object. The detailed description of the exemplary embodiment for comparing and analyzing bio-signal graphs, so as to obtain the weight of the measurement object, has already been provided above with reference to FIG. 4a and FIG. 4b.

Meanwhile, although it is not shown in the flow chart, in addition to the first reference data, the wearable device may separately generate second reference data. The wearable device may use the separately generated second reference data, so as to update the first reference data, or the wearable device may use the separately generated second reference data, so as to obtain the weight of the measurement object along with the first reference data. The detailed description of the same has already been provided above with reference to FIG. 6. Additionally, the wearable device may use the first reference data and/or the measurement data, so as to generate user identification information for identifying the user. The detailed description of the same has already been provided above with reference to FIG. 6.

As described above, the wearable device and the method for controlling the same may have the following advantages. According to an exemplary embodiment, since reference data are being generated with respect to each user, the estimation accuracy in obtaining the weight of the measurement object is increased. Additionally, according to another exemplary embodiment, since reference data respective to multiple reference objects are generated and then compared with the measurement data, the estimation accuracy in obtaining the weight of the measurement object is also increased. Furthermore, according to yet another exemplary embodiment, since the generated data is being used as user identification information, separate user identification information is not required to be inputted in order to ensure security in the wearable device. Finally, according to yet another exemplary embodiment, since user health information may be obtained by comparing multiple data sets, which are generated in accordance with a predetermined time interval, with one another, useful information related to the user's health may be provided.

For simplicity in the description, although each drawing provided herein has been described by being differentiated from one another, the exemplary embodiment may be configured as another exemplary embodiment by combining any one of the above-described drawings with another one of the above-described drawings. Additionally, whenever required by anyone skilled in the art, the scope of the present specification may also include designing a recording medium that can be read by a computer having a program for executing the above-described exemplary embodiments recorded therein.

Moreover, the configuration and method for configuring the above-described exemplary embodiments of the wearable device and the method for controlling the same will not be limited only to the examples presented herein. And, therefore, it will be apparent that the exemplary embodiments of the present specification may be fully or partially modified and combined so as to implement a new exemplary embodiment of the present specification.

Additionally, although the preferred embodiments of presented herein, the present specification will not be limited only to the exemplary embodiments presented herein. And, therefore, it will be apparent to those skilled in the art that various modifications and variations can be made in the present specification without departing from the spirit or scope of the inventions. Thus, it is intended that the present specification covers the modifications and variations of this invention provided they come within the scope of the appended claims and their equivalents, and that the varied embodiments should not be separately interpreted and understood from the technical scope and spirit of the present specification.

Meanwhile, the wearable device and the method for controlling the same of the present specification may be implemented as a processor-readable code in a recording medium, which can be read by the processor being equipped in the network device. The processor-readable storage medium includes all types of recording devices that are configured to store data that can be read by a processor. Examples of the processor-readable storage medium may include a ROM, a RAM, a CD-ROM, an electro-magnetic tape, a floppy disk, an optical data storage device, and so on. Furthermore, the processor-readable recording medium may also include recording media that can be realized in the form of carrier waves, such as transmission via the Internet. Finally, the processor-readable recording medium may be dispersed to a computer system that is connected via network, thereby being capable of storing and executing processor-readable codes by using a dispersion method.

Moreover, in the present specification, the weight may represent an accurate value and may also be considered to include a substantial weight within a constant range. More specifically, the weight mentioned in the present specification may indicate a substantial weight, and a predetermined difference range may exist herein.

Finally, both device invention and method invention are described in the present specification. And, whenever required, the description of both inventions may be supplementarily applied.

What is claimed is:

1. A wearable device, comprising:
   a bio-signal sensor unit configured to sense a bio-signal;
   a storage unit configured to store data; and
   a processor configured to control the bio-signal sensor unit and the storage unit,
   wherein the processor is further configured to:
   generate first reference data including a weight of a first reference object and a first bio-signal generated by holding the first reference object when the first bio-signal is detected,
   generate measurement data including a second bio-signal generated by holding a measurement object when the second bio-signal is detected, and
   obtain a weight of the measurement object by comparing the measurement data with the first reference data.

2. The wearable device of claim 1, wherein the processor is further configured to:
   compare the first bio-signal included in the first reference data with the second bio-signal included in the measurement data, and
   obtain the weight of the measurement object by using a compared result and the weight of the first reference object included in the first reference data.

3. The wearable device of claim 1, wherein the first bio-signal is generated when a position of the first reference object is in a stationary state after the first reference object was held, or
   wherein the second bio-signal is generated when a position of the measurement object is in a stationary state after the measurement object was held.

4. The wearable device of claim 1, wherein the first bio-signal is generated when a position of the first reference object is in a mobile state after the first reference object was held, or wherein the second bio-signal is generated when a position of the measurement object is in a mobile state after the measurement object was held.

5. The wearable device of claim 1, wherein the weight of the measurement object corresponds to a relative weight with respect to the first reference object.

6. The wearable device of claim 1, wherein the first reference object corresponds to an object having a predetermined weight.

7. The wearable device of claim 1, further comprising:
an input sensor unit configured to sense an input of the wearable device,
wherein the processor is further configured to receive the weight of the first reference object by detecting the input and to generate the first reference data.

8. The wearable device of claim 1, wherein the bio-signal sensor unit senses at least one of muscular contraction level, electromyogram, skin conductivity, brainwave, pulse rate, electrocardiogram, blood pressure, blood flow rate, and heart rate of a user wearing the wearable device as the bio-signal.

9. The wearable device of claim 1, wherein the first reference data and the measurement data include at least one of date, time, interval, and place at which each data is generated.

10. The wearable device of claim 1, wherein the processor is further configured to update the first reference data by using the measurement data and the obtained weight of the measurement object.

11. The wearable device of claim 1, wherein the processor is further configured to generate second reference data including a weight of a second reference object and a third bio-signal being generated by holding the second reference object.

12. The wearable device of claim 11, wherein the processor is further configured to obtain the weight of the measurement object by comparing the measurement data with the first reference data and with the second reference data.

13. The wearable device of claim 11, wherein the processor is further configured to:
generate the second reference data when a predetermined period of time has elapsed since the first reference data was generated; and
update the first reference data by using the second reference data.

14. The wearable device of claim 11, wherein the processor is further configured to:
generate the second reference data when a predetermined period of time has elapsed since the first reference data was generated, and
obtain health information of a user wearing the wearable device by using the first reference data and the second reference data.

15. The wearable device of claim 14, wherein the health information includes a level of change in an amount of muscles or body fat of the user.

16. The wearable device of claim 14, wherein the second reference object corresponds to an object having a weight equivalent to the weight of the first reference object.

17. The wearable device of claim 1, wherein the processor is further configured to count a number of lifting the measurement object by detecting the second bio-signal.

18. The wearable device of claim 1, wherein the processor is further configured to generate user identification information by using at least one of the first reference data and the measurement data.

19. The wearable device of claim 18, wherein the processor is further configured to identify a user wearing the wearable device by using the generated user identification information.

* * * * *